(12) United States Patent
Stock

(10) Patent No.: US 8,551,321 B2
(45) Date of Patent: Oct. 8, 2013

(54) PROCESS FOR VERIFYING AN ELECTROCHEMICAL SUBSTANCE IN A GAS SAMPLE

(75) Inventor: Burkhard Stock, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 256 days.

(21) Appl. No.: 12/899,827

(22) Filed: Oct. 7, 2010

(65) Prior Publication Data

US 2011/0139633 A1 Jun. 16, 2011

(30) Foreign Application Priority Data

Dec. 1, 2009 (EP) ..................................... 09177650

(51) Int. Cl.
*G01N 33/497* (2006.01)

(52) U.S. Cl.
USPC ............... 205/775; 73/23.3; 422/84; 600/532

(58) Field of Classification Search
USPC ........... 356/454, 437, 519, 506, 480; 72/23.3, 72/23.2, 73.3; 422/83, 84, 89–92, 98, 119, 422/82.01, 82.02; 600/532; 205/775; 204/229.4–229.8, 406–409
See application file for complete search history.

(56) References Cited

U.S. PATENT DOCUMENTS 5,612,896 A * 3/1997 Stock ............................. 702/24

FOREIGN PATENT DOCUMENTS

DE 43 44 196 C2 6/1995

OTHER PUBLICATIONS webpage: "Integration Methods in Chemistry" available Jun. 1, 2008 from http://www.shodor.org/unchem/math/integrate/index.html.*

* cited by examiner

*Primary Examiner* — J. Christopher Ball
(74) *Attorney, Agent, or Firm* — McGlew and Tuttle, P.C.

(57) ABSTRACT

A process is provided for verifying an electrochemical substance in a gas sample. The process generates in an electrochemical sensor a measured electric value changing over time with a characteristic rising from a reference line to a maximum and again declining to the reference line. The percentage of the electrochemical substance in the gas sample is determined in an analysis circuit by setting a first interval and a second interval in the range of the characteristic after the maximum has been exceeded. The first interval includes the range of the characteristic in the vicinity of the maximum and the second interval includes the range of the maximum in the vicinity of the reference line. The electrochemical substance is determined by determining the ratio of the slopes of the first and second intervals and by comparison with a reference value of the ratio of the slopes of the first and second intervals.

20 Claims, 2 Drawing Sheets

PROCESS FOR VERIFYING AN ELECTROCHEMICAL SUBSTANCE IN A GAS SAMPLE

CROSS REFERENCE TO RELATED APPLICATIONS

This application claims the benefit of priority under 35 U.S.C. §119 of European Patent Application EP 09 177 650.0 filed Dec. 12, 2009, the entire contents of which are incorporated herein by reference.

FIELD OF THE INVENTION

The present invention pertains to a process for verifying an electrochemical substance in a gas sample and to a device for carrying out the process.

BACKGROUND OF THE INVENTION

A process for determining characteristics of an electrochemical substance (electrochemically detectable substance) in a gas sample has become known from DE 43 44 196 C2.

The percentage of the electrochemical substance in the gas sample is calculated in the prior-art process from an integration over the total area enclosed between a reference line and a maximum of a measured physical variable. Partial areas are used for the calculation as partial integrals of the total integral of the total area, from which different characteristics of the substance to be detected, e.g., the concentration percentage in the gas sample or the species of the substance can be determined.

The electrochemical substance is recognized from the comparison of the partial areas, which are formed by the pattern of the curve of a measured electric variable of the measuring cell and the time. The presence of additional chemical substances leads to a slower course of the electrochemical processes. As a result, the profile of the measured electric value over time is changed. The ratio of the area percentages also changes as a result.

It was found in the above mentioned process that aging of the measuring cell as well as a reduction of the temperature lead to an increase in the internal resistance of the measuring cell. As a consequence of this, the electrochemical processes take place more slowly.

Thus, the pattern of the curve of the measured signal changes in the prior-art measuring cell with increasing aging of the measuring cell. Thus, the curve profile becomes flatter and broader in the course of the use time. A similar change in the pattern of the curve of the measured signal also occurs in the presence of additional electrochemical substances. A flatter curve profile may thus result from aging or a lower temperature of the electrochemical measuring cell, but also from the presence of additional electrochemical substances.

SUMMARY OF THE INVENTION

Thus, the basic object of the present invention is to improve an analytical method for a measured electric value of an electrochemical measuring cell such that the concentration percentage of the substance to be detected can be reliably determined with high long-term stability over the use time of the measuring cell.

This object is accomplished by a process for verifying an electrochemical substance in a gas sample and by a device for carrying out the process according to the invention.

The object is accomplished by the slopes of the curve of a measured electric value, which changes over time and generates a characteristic rising from a reference line to a maximum and again declining to the reference line, being analyzed in a range after exceeding the maximum. This is done by setting in a first process step a first interval and a second interval in the range of the characteristic after exceeding the maximum, the first interval comprising the range of the characteristic in the vicinity of the maximum and the second interval comprising the range of the characteristic in the vicinity of the reference line. Furthermore, the ratio of the slopes of the characteristics of the first and second intervals is determined and subsequently compared with a reference value of the ratio of the slopes of the first and second intervals of this electrochemical substance.

The reliability of the measuring result of an electrochemical measuring cell can be advantageously improved hereby. In particular, the reliability of the measuring result can thus be increased in case of application of the electrochemical measuring cell in a breath alcohol measuring device. This applies especially to the effect of additional electrochemical substances on the electrochemical substance to be determined.

Due to the marked improvement of the process according to the present invention, the measuring results of manual electrochemical devices for breath alcohol measurement, which are based on an electrochemical detection method, can also be used for expert opinions given before a court of law. The possibility that the measuring result is distorted by external effects can be ruled out, for example, a defect of the device or based on foreign substances can be ruled out.

In another advantageous embodiment of the process according to the present invention, the first interval may range from a percentage of the maximum equaling about 90% to a percentage of the maximum equaling about 80%. Furthermore, the second interval may advantageously extend from a percentage of the maximum equaling about 20% to a percentage of the maximum equaling about 10%.

The electrochemical substance to be detected includes, especially for breath alcohol measurement, ethyl alcohol. The reference value of the ratio of the slopes of the first and second intervals of the electrochemical substance to be determined is determined during the first calibration of the electrochemical sensor.

Furthermore, means for storing the reference value are provided.

In another advantageous embodiment of the process according to the present invention, the measuring result is defined as being invalid if the reference value deviates from the determined value of the ratio of the slopes of the characteristics of the first and second intervals. As an alternative hereto, a reliable limit value may be provided and the measuring result can be utilized in case the reliable limit value is exceeded.

In another alternative of the process according to the present invention, a correction of the measuring result can be performed if the reference value deviates from the value determined from the ratio of the slopes of the characteristics of the first and second intervals or exceeds a reliable limit value. Correction of the measuring result can be performed now by reducing the percentage of the electrochemical substance in the gas sample. A deviation of the reference value from the value determined from the ratio of the slopes of the characteristics of the first and second intervals can be advantageously signaled visually or acoustically.

The process according to the present invention may be used in a device for alcohol measurement, especially in a breath alcohol measuring device.

The present invention will be explained in more detail with reference to the drawings attached, in which identical reference numbers designate identical features. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
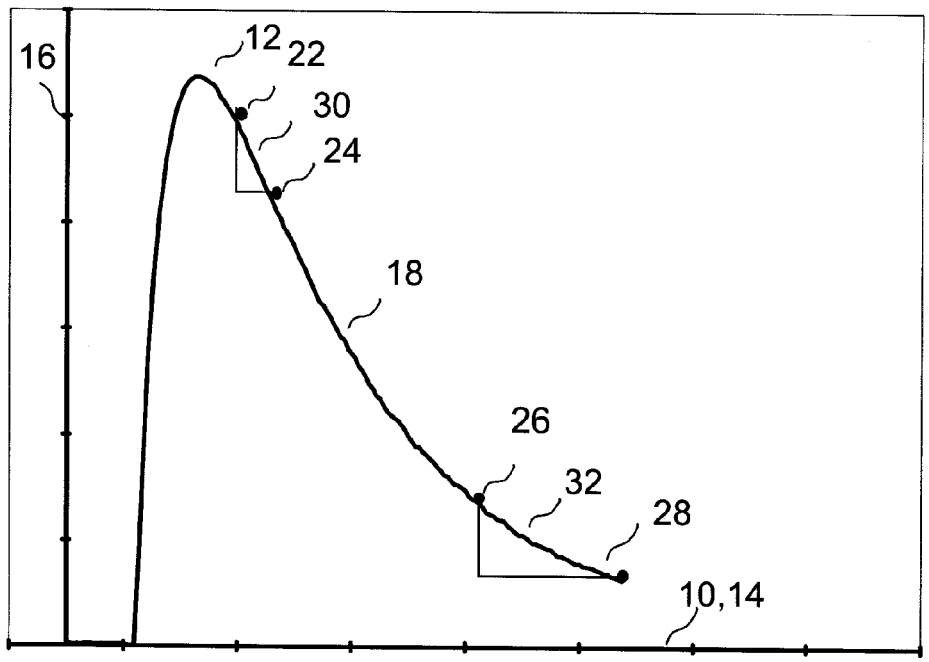
FIG. 1 is a diagram of the course over time of the measured electric value of an electrochemical sensor for a gas sample of ethyl alcohol.

Referring to the drawings in particular, FIG. 1 shows the curve of a current value of an electrochemical sensor 48 (shown in FIG. 3) after admission of a gas sample 42 of ethyl alcohol along a time axis 14 and a current axis 16. The current value of the electrochemical sensor 48, which changes over time, rises steeply from a reference line 10 to a maximum 12 and drops again exponentially from the maximum 12 to the reference line 10. Characteristic 18 shown in FIG. 1 corresponds to the current/time characteristic of ethyl alcohol. An experimental analysis revealed that the range of the characteristic between the maximum 12 and the reference line 10 is a superimposition of a plurality of exponential functions with different fall times, which are caused by a multistep reaction of ethyl alcohol ultimately to $CO_2$ and water. Furthermore, it is seen that the electrochemical processes take place more slowly in case of aging of the electrochemical sensor 48 as well as at lower temperatures. However, the basic shape of the current/time characteristic 18 remains intact.

Figure 2:
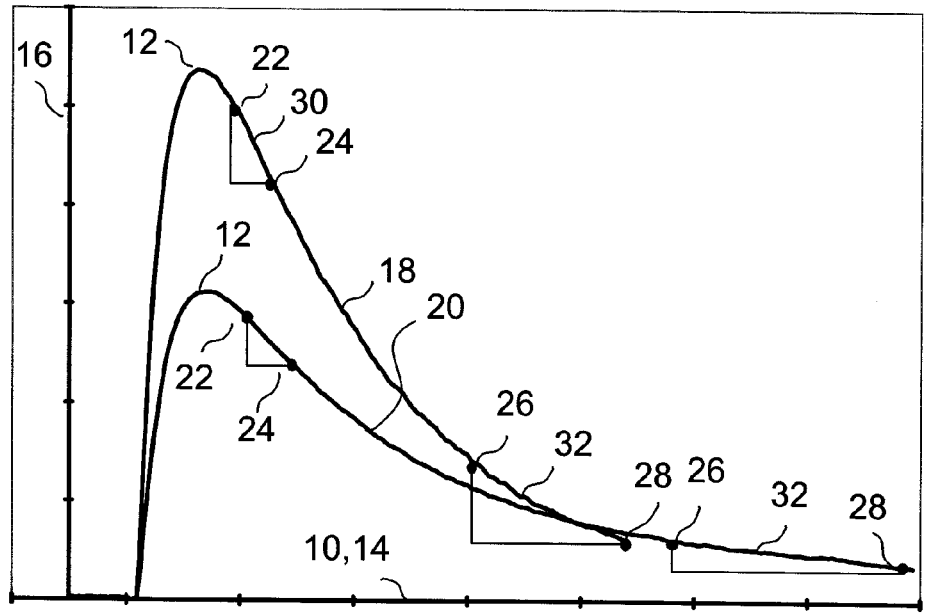
FIG. 2 is a diagram of the course over time of the measured electric values of an electrochemical sensor for a gas sample of ethyl alcohol and a gas sample of an ethyl alcohol/methyl alcohol mixture.

Another current/time characteristic 20 for a mixture of ethyl alcohol and methyl alcohol is shown in FIG. 2 in addition to the current/time characteristic 18 of ethyl alcohol. This mixture of ethyl alcohol and methyl alcohol has different reaction steps with a different time characteristic. The current/time characteristic 20 of the mixture no longer has affinity with that of ethyl alcohol. A decline of the current/time characteristic of methyl alcohol after the maximum 12 has been exceeded drops markedly more flatly, because the oxidation of methyl alcohol takes place over steps different from those of the oxidation of ethyl alcohol.

In the application of the process according to the present invention, a first interval 30 and a second interval 32 are set in a first step in the range of the characteristic after the maximum 12 is exceeded. The first interval 30 is formed here by a current value 22 at a time 1 and a current value 24 at a time 2. The second interval is formed by a current value 26 at a time 3 and a current value 28 at a time 4. Current value 22 advantageously corresponds to a percentage of about 90% of maximum 12 and current value 24 to a percentage of about 80% of maximum 12. Current value 26 corresponds approximately to 20% of maximum 12, and current value 28 corresponds approximately to 10% of maximum 12.

The ratio of the slopes of the current/time characteristics 18 of ethyl alcohol in the first and second intervals 30, 32 is determined in another process step. The slope S1 of the first interval 30 is obtained corresponding to the formula:

$$S1 = (\text{current value } 22 - \text{current value } 24)/(\text{time } 1 - \text{time } 2)$$

The slope S2 of the second interval 32 is obtained analogously to this corresponding to the formula:

$$S2 = (\text{current value } 26 - \text{current value } 28)/(\text{time } 3 - \text{time } 4)$$

A ratio of the slopes S is thus obtained corresponding to the formula:

$$S = S1/S2.$$

The ratio of the slopes S thus determined is compared in a next step with a reference value Sref of the ratio of the slopes of the first and second intervals 30, 32 of this electrochemical substance according to the formula:

$$K = S/S_{ref}.$$

Comparative value K is independent from the age of the electrochemical sensor 48. Comparative value K depends only on the electrochemical substance reacted in the electrochemical sensor 48. the reference value $S_{ref}$ of the ratio of the slopes of the first and second intervals 30, 32 of the electrochemical substance to be determined is determined during a first calibration of the electrochemical sensor 48, in general, after the manufacture thereof, and then stored. If a gas sample 42 of ethyl alcohol is admitted to the electrochemical sensor 48, a comparative value of K=1 is obtained. If the electrochemical substance methyl alcohol is added to the gas sample 42 of ethyl alcohol, the comparative value K will increase correspondingly. The current/time characteristic 20 will change correspondingly compared to the current/time characteristic 18 of ethyl alcohol.

The characteristic 20 of ethyl alcohol and methyl alcohol, which is shown as an example in FIG. 2, corresponds to a mixture of 120 ppm of ethyl alcohol and 60 ppm of methyl alcohol. The current signal drops correspondingly more flatly after the maximum 12 of the current value, because the reaction of methyl alcohol takes place substantially more slowly than the reaction of ethyl alcohol. The percentage of the characteristic before the maximum 12 is determined by ethyl alcohol, and the percentage after the maximum 12 is determined by methyl alcohol. Based on the fact that the current/time characteristic 20 differs from the current/time characteristic 18, the comparative value K increases correspondingly. The comparative value corresponds to K=1.6 for the example being shown.

In case of a deviation of the comparative value K from 1, the measuring result can be defined as being invalid. As an alternative to this, a limit value, for example, 1.2, may be provided as well. The measuring result is correspondingly defined as invalid in case the limit value is exceeded. In another alternative, the measuring result can be correspondingly corrected with a rising comparative value K, and, for example, a limitation may be performed in terms of a percentage according to the following formula:

$$\text{Measuring result} = \text{Measuring result} * (1 - a * (K - 1)).$$

A comparative value K equaling 1 is obtained in case of the presence of ethyl alcohol only in the gas sample. The comparative value K will also increase correspondingly with increasing percentage of another electrochemical substance, for example, methyl alcohol. The measuring result is correspondingly reduced, and an indicator of the reduction can be set with a factor a. The following result is obtained for the above-described example with a factor of a=0.3:

Measuring result=Measuring result*(1−0.3*(1.6−1))

Measuring result=Measuring result*0.82.

Thus, the process according to the present invention represents a reliable process for verifying an electrochemical substance in a gas sample based on the independence from the aging process of the electrochemical sensor 48 as well as from the measuring temperature.

Figure 3:
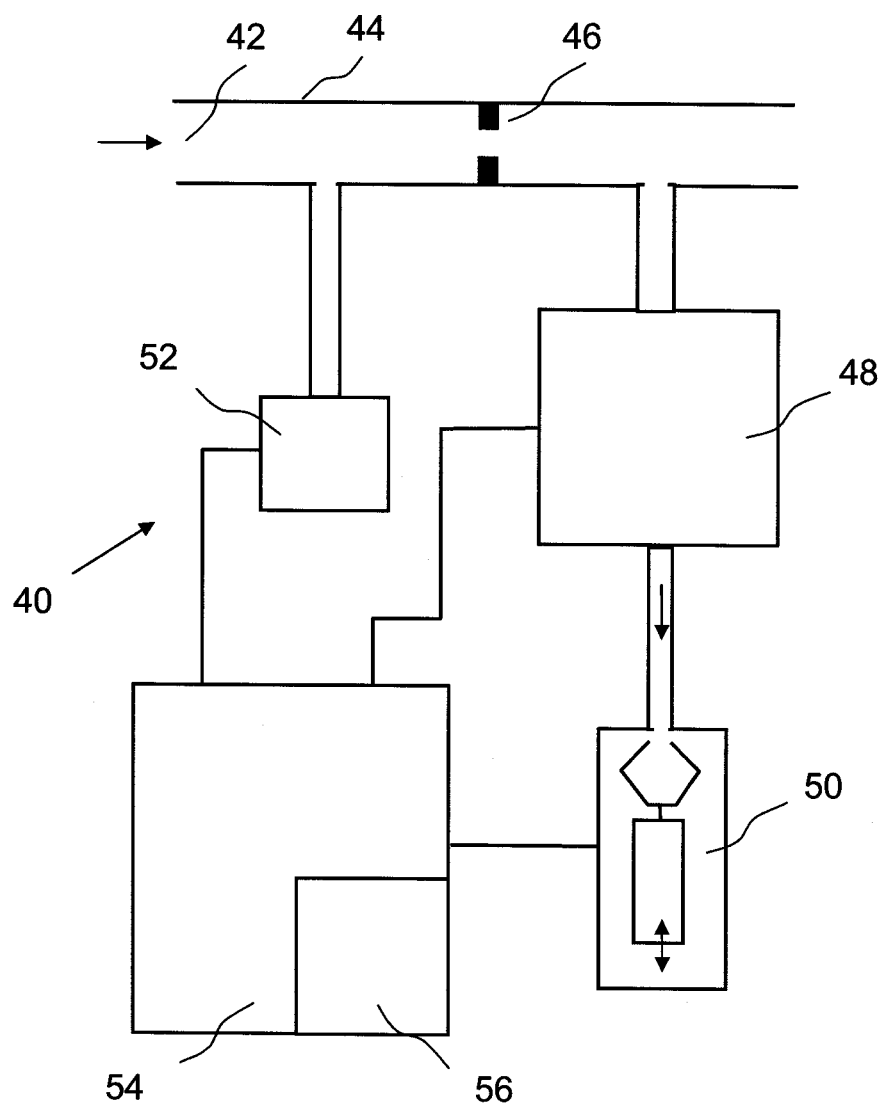
FIG. 3 is a schematic view of a device according to the invention for carrying out the process according to the invention.

FIG. 3 schematically shows the design of a device for carrying out the process based on the example of a breath alcohol measuring device 40.

The breathing air of a test subject flows as a gas sample 42 through a mouthpiece 44. The gas sample 42 now generates a pressure drop at a diaphragm 46. The gas sample 42 reaches both a pressure sensor 52 and the electrochemical sensor 48. The pressure sensor 52 continuously measures the pressure when a sample is released by the test subject and calculates from this the volume of gas sample 42 given by the test subject. After giving a defined volume of gas sample 42, a control unit 54 starts a pump 50. The gas sample 42 is drawn as a result into the electrochemical sensor 48. A corresponding breath alcohol concentration is determined by the control unit 54 from the current signal of the electrochemical sensor 48. The reference value of the ratio of the slopes of the first and second intervals 30, 32 of the electrochemical substance to be determined is stored in a memory unit 56, which may be designed as an integral part of control unit 54.

While the present invention was described with reference to the preferred exemplary embodiments, various changes and modifications are obvious to the person skilled in the art. All these changes and modifications shall fall within the scope of protection of the claims presented.

While specific embodiments of the invention have been described in detail to illustrate the application of the principles of the invention, it will be understood that the invention may be embodied otherwise without departing from such principles.

APPENDIX—LIST OF REFERENCE NUMBERS

10 Reference line
12 Maximum
14 Time axis
16 Current axis
18 Current/time characteristic of ethyl alcohol
20 Current/time characteristic of a mixture of ethyl alcohol and methyl alcohol
22 Current value at time 1
24 Current value at time 2
26 Current value at time 3
28 Current value at time 4
30 First interval
32 Second interval
40 Breath alcohol measuring device
42 Gas sample
44 Mouthpiece
46 Diaphragm
48 Electrochemical sensor
50 Pump
52 Pressure sensor
54 Control unit
56 Memory unit

What is claimed is:

1. A process for verifying an electrochemical substance in a gas sample, the process comprising the steps of:
in an electrochemical sensor generating a measured electric value changing over time with a characteristic rising from a reference line to a maximum and again dropping to the reference line;
determining, from measured electric value, a percentage of the electrochemical substance in the gas sample in an analysis circuit by the following steps:
setting of a first interval and a second interval in the range of the characteristic after the maximum has been exceeded, wherein the first interval comprises the range of the characteristic in the vicinity of the maximum and the second interval comprises the range of the characteristic in the vicinity of reference line;
determining a ratio of the slopes of the first and second intervals; and
comparing the ratio of the slopes of the first and second intervals of this electrochemical substance with a reference value.

2. A process in accordance with claim 1, wherein the first interval extends from a percentage of the maximum equaling about 90% to a percentage of the maximum equaling about 80%.

3. A process in accordance with claim 1, wherein the second interval extends from a percentage of the maximum equaling about 20% to a percentage of the maximum equaling about 10%.

4. A process in accordance with claim 1, wherein the measured electric value comprises a current value.

5. A process in accordance with claim 1, wherein the electrochemical substance comprises ethyl alcohol.

6. A process in accordance with claim 1, wherein the reference value of the ratio of the slopes of the first and second intervals of the electrochemical substance to be determined is determined during the first calibration of the electrochemical sensor.

7. A process in accordance with claim 6, further comprising the step of:
providing a means for storing the reference value.

8. A process in accordance with claim 1, wherein a measuring result is defined as being invalid if the reference value deviates from the value determined in process step of determining the ratio of the slopes of the first and second intervals.

9. A process in accordance with claim 1, wherein the measuring result is defined as being invalid if a deviation of the reference value from the value determined in the process step of determining the ratio of the slopes of the first and second intervals exceeds a limit value.

10. A process in accordance with claim 1, wherein a correction of the measuring result is performed if the reference value deviates from the value determined in process step of determining the ratio of the slopes of the first and second intervals or a deviation of the reference value from the value determined in the process step of determining the ratio of the slopes of the first and second intervals exceeds a limit value.

11. A process in accordance with claim 10, wherein a percentage of the electrochemical substance in the gas sample is reduced.

12. A process in accordance with claim 1, wherein a deviation of the reference value from the value determined in process step of determining the ratio of the slopes of the first and second intervals is signaled.

13. A device for verifying an electrochemically detectable substance in a gas sample, the device comprising:

an electrochemical sensor generating a measured electric value changing over time with a characteristic rising from a reference line to a maximum and again dropping toward the reference line; and an analysis circuit determining device for determining a percentage of the electrochemical substance in the gas sample from the measured electric values, the analysis circuit setting a first interval and a second interval in the range of the characteristic after the maximum has been exceeded, wherein the first interval comprises the range of the characteristic in the vicinity of the maximum and the second interval comprises the range of the characteristic in the vicinity of reference line, determining a ratio of the slopes of the first and second intervals and comparing the ratio of the slopes of the first and second intervals of this electrochemical substance with a reference value.

14. A device in accordance with claim 13, wherein the first interval extends from a percentage of the maximum equaling about 90% to a percentage of the maximum equaling about 80%.

15. A device in accordance with claim 13, wherein the second interval extends from a percentage of the maximum equaling about 20% to a percentage of the maximum equaling about 10%.

16. A device in accordance with claim 13, wherein:
the measured electric value comprises a current value;
the electrochemical substance comprises ethyl alcohol; and
the reference value of the ratio of the slopes of the first and second intervals of the electrochemical substance to be determined is determined during the first calibration of the electrochemical sensor.

17. A device in accordance with claim 13, further comprising: a reference value storage means for storing one or more reference value.

18. A device in accordance with claim 13, wherein a measuring result is defined as being invalid if one of:
the reference value deviates from the value determined in process step of determining the ratio of the slopes of the first and second intervals; and
a deviation of the reference value from the value determined in the process step of determining the ratio of the slopes of the first and second intervals exceeds a limit value.

19. A device in accordance with claim 13, further comprising a signaling device wherein a deviation of the reference value from the value determined in process step of determining the ratio of the slopes of the first and second intervals is signaled with the signaling device.

20. A breath alcohol measuring device for measuring breath alcohol in a gas sample, the breath alcohol measuring device comprising:
an electrochemical sensor generating a measured electric value changing over time with a characteristic rising from a reference line to a maximum and again dropping toward the reference line; and
a control including an analysis circuit determining a percentage of alcohol in the gas sample from the measured electric values, the analysis circuit setting a first interval and a second interval in the range of the characteristic after the maximum has been exceeded, wherein the first interval comprises the range of the characteristic in the vicinity of the maximum and the second interval comprises the range of the characteristic in the vicinity of reference line, determining a ratio of the slopes of the first and second intervals and comparing the ratio of the slopes of the first and second intervals of this electrochemical substance with a reference value.

* * * * *